United States Patent [19]
Phillips et al.

[11] Patent Number: 5,187,154
[45] Date of Patent: Feb. 16, 1993

[54] DIAGNOSIS AND TREATMENT OF HUMANS WITH DIABETES OR AT RISK TO DEVELOP DIABETES

[75] Inventors: William Phillips; Joyce G. Schwartz, both of San Antonio, Tex.

[73] Assignee: Board of Regents, The University of Texas System, Austin, Tex.

[21] Appl. No.: 626,579

[22] Filed: Dec. 13, 1990

[51] Int. Cl.$^5$ .................. A61K 37/00; A61K 49/00
[52] U.S. Cl. .................. 514/12; 514/866; 424/9
[58] Field of Search .................. 514/12, 866; 424/9

[56] References Cited

PUBLICATIONS

Dorland's Illustrated Medical Dictionary, 26th ed. (W. B. Saunders Co. 1990) at 368–369.
Conn's 1989 Current Therapy, Robert E. Rakel (Ed.) (W. B. Saunders Co.) at 482–498.
Eisenbarth, New Eng. J. Med. (May 1986) 1360–1368.
Brown et al. Can. J. Phys. Pharmacol. (1983) 283–289 Abstract.
Horowitz et al. Diabetologia (1989) vol. 32 151–159.
Liddie et al J. Clin Inves vol. 77 (1986) 992–996.
Jenkins et al Diabetes vol. 39 (Jul. 1990).
Granneman CA 102(7) 60260u (1984).
Barnett CA 108(17) 148220r (1988).
Thompson et al., "Gastric Emptying as a Determinant of the Oral Glucose Tolerance Test", Gastroenterology, 82:51–55 (1982).
Brener et al., "Regulation of the Gastric Emptying of Glucose", Gastroenterology, 85:76–82 (1983).
Keshavarzian, et al., "Gastric Emptying in Patients with Insulin-Requiring Diabetes Mellitus", Am. J. Gastroenterology, 82(1):29–35 (1987).
Campbell, et al., "Gastric emptying in diabetic autonoic neuropathy", Gut, 18:462–467 (1977).
Horowitz, et al., "Gastric and oesophageal emptying in patients with type 2 (non–insulin–dependent) diabetes mellitus", Diabetologia, 32:151–159 (1989).
Smout, J. J. P. M., Z. Gastroenterologie 24(Suppl. 2):45–54 (1986).
Pellegrini, et al., "Diagnosis and Treatment of Gastric Emptying Disorders", Am. J. Surg., 145:143–151 (1983).
Akkermans, et al., "Neural and Hormonal Control of Pyloric Sphincter Function", Gastroenterol. Suppl., 24:27–31 (1989).
Schwartz, et al., "Revision of the Oral Glucose Tolerance Test: A Pilot Study", Clinical Chemistry, 36(1):125–128 (1990).
Liddle, R. A., Federal Research in Progress, National Institute of Diabetes and Digestive and Kidney Diseases (1990).
Chaudhuri, T. K. and Fink, S., "Update: Pharmaceuticals and Gastric Emptying", Am. J. Gastroenterology, 85(3):223–231 (1990).
Liddle, et al., "Regulation of Gastric Emptying in Humans by Cholecstokinin", J. Clin. Invest., 77:992–996 (1986).

(List continued on next page.)

Primary Examiner—Merrell C. Cashion, Jr.
Assistant Examiner—B. Celsa
Attorney, Agent, or Firm—Arnold, White & Durkee

[57] ABSTRACT

The invention relates to a method of diagnosing and treating individuals with diabetes or at risk to develop diabetes mellitus. In particular, gastric emptying determinations are used to assess risk. Risk or early symptoms associated with subsequent development of diabetes mellitus may be controlled or alleviated by delaying gastric emptying. Delay or inhibition of gastric emptying is sufficient to restore gastric emptying within normal ranges as determined by restoration of typical glucose metabolic parameters such as blood glucose and insulin levels to normal or near normal ranges. The method is also useful in prophylactic treatment of individuals at high risk to develop diabetes mellitus, such as the obese, those with a family history of diabetes and those of particular ethnic and minority groups.

4 Claims, 10 Drawing Sheets

OTHER PUBLICATIONS

Liddle, et al., "Physiological Role for Cholecystokinin in Reducing Post-prandial Hyperglycemia in Humans", *J. Clin. Invest.*, 81:1675–1681 (1988).

Jenkins, et al., *Diabetes*, 39:775–780 (1990).

Cohen, et al., "High Prevalence of Diabetes in Young Adulg Ethiopian Immigrants to Israel", *Diabetes*, 37:824–827 (1988).

Rowland, M. and Tozer, T. N., in Clinical Pharmacokinetics: Concepts and Applications, Second Edition, 117–129 (1989).

Jenkins, et al., "Metabolic Advantages of Increased Meal Frequency", *The New England Journal of Medicine*, 321(14):929–934 (1989).

Cowen, R., "Seeds of Protection: Ancestral menus may hold a message for diabetes-prone descendants", *Science News*, 137:350–351 (1990).

Vinik, A. I. and Jenkins, J. A., "Dietary Fiber in Management of Diabetes", *Diabetes Care*, 11(2):160–173 (1988).

Fiorucci, et al., Medline Abstract, *Dig. Dis. Sci.*, 35(9):1089–97 (1990).

Dialog Search Abstracts, Items 1–8, Oct. 15, 1990.

Dialog Search Abstracts, Items 1–8, Oct. 10, 1990.

DIAGNOSIS AND TREATMENT OF HUMANS WITH DIABETES OR AT RISK TO DEVELOP DIABETES

The Government may have certain rights in the invention pursuant to grant No. 2-S07-RR07187-11.

BACKGROUND OF THE INVENTION

1. Field of the Invention

The invention relates to a method of identifying and treating patients at risk or in early onset of diabetes mellitus by first determining gastric emptying patterns and then treating with an appropriate drug. Treatment comprises administration of a pharmaceutical preparation having the ability to inhibit or block gastric emptying. In particular, drugs that affect gut motility are useful as a method of treatment in reducing gastric emptying rates to a near normal range, effectively slowing delivery of glucose to the duodenum and reducing hyperglycemia.

2. Description of Related Art

In recent years the role of the stomach in glucose homeostasis has become recognized (1). In 1982, Thompson described gastric emptying as an important determinant of the oral glucose tolerance test and suggested that the glucose tolerance test could be used to assess gastric emptying. In 1983 Brener et al. (2) described characteristic gastric emptying of glucose solutions in normal human subjects In their studies they discovered that glucose empties from the stomach in a constant and linear fashion at an average of 2.13 kcal/min regardless of the concentration of the glucose solution Prior to this study, it was widely believed that all liquids emptied in an exponential manner. It is Brener's hypothesis that a dynamic "closed loop" feedback interrelationship exists between the stomach and the duodenum to control the delivery of calories from the stomach.

Keshavarzian et al. (3) have studied gastric emptying in a heterogeneous group of diabetics with insulin-dependent diabetes mellitus and non-insulin dependent diabetes mellitus who had been diagnosed for more than 5 years. Although Keshavarzian emphasized the delay in gastric emptying, particularly with solids, some diabetic subjects in the study exhibited a more rapid gastric emptying compared to controls. Liquid gastric emptying was generally the same for both the controls and diabetics with the gastric half-emptying time (t½) showing no significant difference. It was noted that some of the patients exhibited abnormally fast emptying, but no significance was associated with the observation.

Campbell et al. (4) described delayed gastric emptying in 10 of 12 diabetic subjects. Although the majority of the patients showed delayed gastric emptying, two of the subjects exhibited more rapid gastric emptying rates compared with controls.

Horowitz et al. (5) described delayed gastric and esophageal emptying in 20 subjects with non-insulin dependent diabetes mellitus. The duration of known diabetes in the subjects ranged from 1-20 years. Although two of the subjects exhibited more rapid than normal liquid gastric emptying, the group of 20 as a whole exhibited delayed liquid gastric emptying (t½ slower than in normal patients, $p<0.05$). There was significant delay of solid food emptying in these patients (increased retention of solid food at 100 min, $p<0.001$).

Gastric emptying has been studied as a non-invasive diagnostic tool as an indicator of metabolic and neural disturbances. For example, chronic forms of gastric stasis can be caused by innervation abnormalities in diabetics with autonomic neuropathy (6). Many other conditions have been studied, including those in patients who had stomach operations or diseases of the gastrointestinal tract. Generally, the majority had delayed gastric emptying (7). In particular, delayed gastric emptying appears to be a phenomenon associated with diabetes. It has been recognized that by delaying nutrient absorption, glucose disposal and insulin economy may be enhanced (14).

Methods of regulating pyloric functions are known in the art. Diabetic gastroparesis and hypertrophic pyloric stenosis are examples of conditions successfully treated (8); delayed gastric emptying has been treated with drugs that accelerate the emptying process, for example metoclopramide or domperidone (11). An opposite effect is shown by Propantheline and opiates which delay gastric emptying (11).

There is some information on the effects of different compounds on enzyme components of pancreatic secretion, for example, the role of cholecystokinin (CCK) (12) and possible regulatory control by other gut hormones, such as VIP which stimulate insulin release from the pancreas (9). It is known that CCK has a significant role in regulating glucose homeostasis in humans (13) and that it delays gastric emptying and reduces hyperglycemia (14). However, the connection between CCK secretion on gastric emptying and insulin release in normal and diabetic patients has not yet been fully evaluated (10).

Studies so far reported indicate that in diabetic patients, delayed gastric emptying is typical. However, until now, there was no realization that certain classes of patients, those not yet manifesting diabetes, those at risk to develop diabetes and those in early stages of diabetes or having non-insulin dependent diabetes, exhibit abnormally rapid gastric emptying. It was this unexpected and surprising discovery that led to the development of a method of a simple treatment By delaying gastric emptying in this group of patients at high risk to develop diabetes, insulin and plasma glucose levels may be maintained at levels much closer to normal levels. This is a first and significant step in early treatment of those at risk for developing debilitating forms of diabetes, even insulin-dependent diabetes, and may delay or forestall completely the usual progress of the disease.

SUMMARY OF THE INVENTION

The invention is based on the unexpected and surprising discovery that early non-insulin dependent diabetics exhibit significantly more rapid gastric emptying than normal controls. This finding forms the rationale for methods of diagnosis and for treatments designed to delay the onset of symptomatic diabetes and possibly to alter the course of the disease. Treatment is based on the use of compounds known to delay gastric emptying, several of which may be employed.

In general, the invention relates to a method of restoring or maintaining glucose metabolic indicators at normal or near-normal levels in an animal or human exhibiting rapid gastric emptying. The method utilizes a substance that will alter gastric emptying and is given in an amount to delay gastric emptying so that normal or near normal emptying rates are attained.

Glucose metabolic indicators relate to interconnected metabolic events. Such parameters include blood glucose levels, blood insulin levels, post prandial glucose and insulin levels, hemoglobin AlC, C-peptide, quantitation of insulin resistance and blood levels of gastric inhibitory peptide (GIP) and cholecystokinin (CCK). One or more of these parameters may exceed normal range without indication to the individual that altered metabolic patterns are developing. These patterns are frequently very early symptoms of diabetes mellitus. For example, blood glucose levels may be high and sugar may be present in the urine. An individual may experience increased thirst and frequency in urination or, in females, vaginal yeast infections without awareness that a health problem exists or is developing. Some of these subjects may exhibit rapid gastric emptying. Rapid gastric emptying is known to affect several parameters relating to the feedback controlling pyloric contraction. The process is complex, but delaying gastric emptying appears to slow delivery of glucose to the duodenum thereby reducing postprandial hyperglycemia. Therefore, in delaying gastric emptying, a treatment is provided which may control the development or at least delay the onset of symptoms that are frequently associated with the onset of diabetes mellitus.

Diabetes mellitus in its early stages may exhibit symptoms that are virtually unnoticed. As the disease develops, later stages may include problems with vision, neuropathy and a marked increase in the number of infections. Later stages of the disease may be associated with loss of vision and atherosclerosis, the latter resulting in circulatory problems, including coronary heart disease.

A particular aspect of the invention therefore is the treatment of a mammal, particularly a human, exhibiting rapid gastric emptying and also showing signs of an early or prediabetic condition, such as elevated blood glucose levels, glycosuria or high levels of endogenous insulin. Using this method of treatment, one first identifies an early or prediabetic condition in an individual. In the more usual circumstance, gastric emptying studies are performed after these symptoms appear; however, some groups of individuals are known to be at risk to develop diabetes. These groups include the morbidly obese, those with a family history of diabetes and most particularly certain ethnic or minority groups, including Hispanics, Eskimos, American Indians, Asian Indians, Chinese, Japanese, Polynesians and those of Jewish descent. In such cases, prudent medical practice would indicate a test of gastric emptying rates. Individuals exhibiting abnormally rapid gastric emptying would then be treated with a therapeutically effective dose of a gastric emptying inhibiting substance. This will be an amount sufficient to alleviate or eliminate symptoms associated with early or prediabetes, particular symptoms including elevated blood glucose and insulin levels, insulin resistance, increased susceptibility to infection and/or glycosuria while also maintaining gastric emptying within normal levels. Individuals at risk or in early stages of diabetes may generally be identified by measuring blood glucose and insulin peak levels after glucose administration.

Any of a number of known gastric emptying inhibiting substances may be used to delay gastric emptying, including gut hormones and analogs, aluminum hydroxide compounds, opiates, estrogens, trypsin inhibitors and tricyclic compounds. Some useful polypeptides might include bombesin, somatostatin, secretin, gastric inhibitory peptide (GIP), VIP, glucagon or gastrin. Propantheline is recognized as delaying gastric emptying. Trypsin inhibitors would be expected to be useful, including Bowman-Birk inhibitor and Camostate. A most preferred substance is cholecystokinin, well studied in humans nd known to effectively delay gastric emptying. Other compounds delaying gastric emptying may be used, including substances that act directly to stimulate a feedback which effectively delays gastric emptying.

The invention is also envisioned as useful in assessing risk of diabetes mellitus in subjects who do not show any abnormalities in glucose metabolism but who have other factors which experience has shown indicate a tendency to develop diabetes mellitus. For example, the morbidly obese, those with a family history of diabetes, those with mature onset diabetes. Non-insulin dependent diabetes is typically seen in individuals over 30 years of age who are able to control the diabetes through diet or oral hypoglycemic drugs.

Another risk group is women who develop diabetes during pregnancy, often distinguished as gestational diabetes because it may first appear to develop during pregnancy. Babies from these pregnancies have an increased risk of birth defects. Rapid gastric emptying would indicate a potential to develop high blood sugar. Control through delaying of gastric emptying might prevent detrimental effects on the fetus during the pregnancy.

Gastric emptying rates may be measured using dye dilution methods and x-ray images after a barium-loaded meal. More preferable techniques include sonography, electrical impedance or scintigraphic methods which are rapid and noninvasive. A most preferable method is scintigraphic determination of ingested $^{99m}$technetium-sulfur colloid using low energy gamma cameras.

Yet another aspect of the invention is a pharmaceutical composition which combines insulin and cholecystokinin in a vehicle suitable for injection This may be saline, a suitable buffer such as phosphate or acetate, an oil-based vehicle or the like. pH modifying substances may be added if necessary to maintain near-neutral or slightly acidic pH. A most preferable mode of injection is intramuscular or subcutaneous because this is normally the mode by which most diabetics self-administer insulin. This composition would be suitable for patients who require insulin and exhibit rapid gastric emptying.

The invention also comprises a pharmaceutical composition of a compound that delays gastric emptying and an oral hypoglycemic in an orally acceptable pharmaceutical formulation. Pharmaceutically acceptable formulating agents include powders, granules, capsules, coated tablets, syrupy preparations and aqueous suspensions. Formulating agents employed may be solid or liquid, including but not limited to such solids as calcium phosphate, calcium carbonate, dextrose, sucrose, dextrin, sucrose ester, starch, sorbitol, mannitol, crystalline cellulose, talc, kaolin, synthetic aluminum silicate, carboxymethyl cellulose, methylcellulose, cellulose acetate phthalate, alginates, polyvinyl pyrrolidone, polyvinyl alcohol, gum arabic, tragacanth gum, gelatin, bentonite, agar powder, shellac, Tween 80, carrageenans and psyllium. Flavor enhancers may be added to oral preparations, including taste masking substances such as sweeteners and citrus flavors. Other additives, including color, preservatives, bulk or antifoam agents may also be included in the formulation. Examples of compounds that delay gastric emptying and may be administered orally are trypsin inhibitors, preferably Bowman-Birk inhibitor or Camostate. These may be mixed with any suitable oral hypoglycemic indicated for the patient, such as chlorpropamide, tolbutamide, tolazamide, glipizide or glyburide.

DESCRIPTION OF THE PREFERRED EMBODIMENT

Subjects

Six subjects with early NIDDM (diagnosed for less than two years) and six sex and age matched nondiabetic subjects underwent gastric emptying studies. The subjects (10 males, 2 females) ranged in age from 35 to 62 years of age. Five of the six subjects with NIDDM were Hispanic Americans, one an Iranian. All 6 non-diabetic subjects were non-Hispanic Caucasians with normal fasting glucose values. The subjects with NIDDM had been previously diagnosed as being diabetic using a 75 g oral glucose tolerance test (OGTT) with blood sampled fasting and at 2 hr according to current WHO criteria. All the subjects with NIDDM were taking oral hypoglycemic medication which they discontinued the evening prior to the study. All studies were begun between 7-8 am following a 12 hr fast.

Statistical Methods

The data were analyzed using a paired t-test. The gastric half-emptying time for each patient was calculated by linear interpolation.

Materials

Sources of drugs and materials are as indicated. Bowman-Birk trypsin inhibitor is available from Nestech, Ltd, Devey, Switzerland. ONA Pharmaceuticals, Ltd., Osaka, Japan, may be contacted for availability of another trypsin inhibitor, Camostate.

The following examples are presented for illustrative purposes and are not intended to be limiting

EXAMPLE 1

Gastric Emptying in Human Subjects

Gastric emptying studies utilizing a gamma camera (Scintronix USA Inc., Woburn MA, USA) were performed with a modified 0.62 M (50g glucose in 450 ml water) glucose solution. The use of this glucose solution in gastric emptying has been previously studied (9). Approximately 200 µCi of 99 metastable technetium sulfur colloid ($^{99m}$Tc-SC, CIS-US, Bedford, MA, USA) were added and mixed with the glucose solution. The subjects drank the glucose solution in its entirety in a 5 minute span shortly after the $^{99m}$Tc-SC had been added to the solution.

The subjects were then placed in a semi-reclining position (45 degrees from horizontal) and the gamma camera was positioned anteriorly. Only anterior views were used in calculating the gastric emptying since it has been shown (12) that the geometric means of the anterior and posterior projections, using liquid meals, were very similar to those of the anterior views alone. Data were collected continuously and summed at 60 second intervals. Images were acquired during an interval of 120 minutes. Blood samples were drawn at 15 minute intervals beginning just prior to ingestion of the glucose solution and ending at 120 minutes. The blood was collected in vacutainer tubes containing potassium oxalate and sodium fluoride (Becton Dickinson Vacutainer Systems, Rutherford, N.J., USA). Glucose analysis was performed on a Paramax instrument (Baxter Healthcare Corp., Irvine, CA, USA).

The Scintronix gamma camera was used with low energy, all purpose collimator at a 20% window setting centered at 140 keV. The camera was connected to a Medical Data Systems Computer (An Arbor, MI, USA). Counts in the stomach region of interest were calculated in each 60 second image. After correcting for radioactive decay, the count rates were converted to percentage of the maximum count rate recorded.

Figure 1:
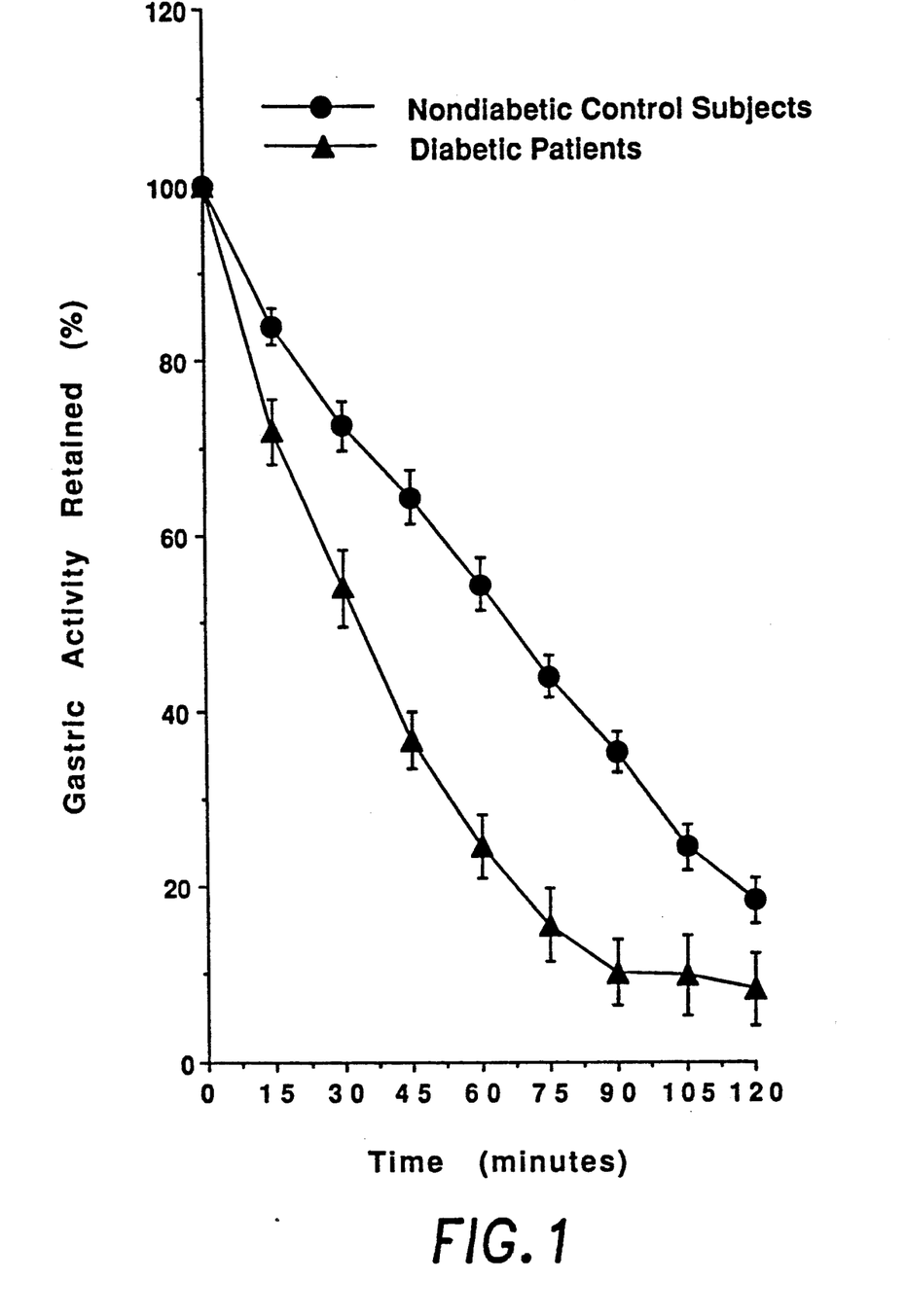
FIG. 1 shows the gastric emptying pattern of six subjects with non-insulin dependent diabetes mellitus and an equal number of age and sex-matched controls.
Figure 2:
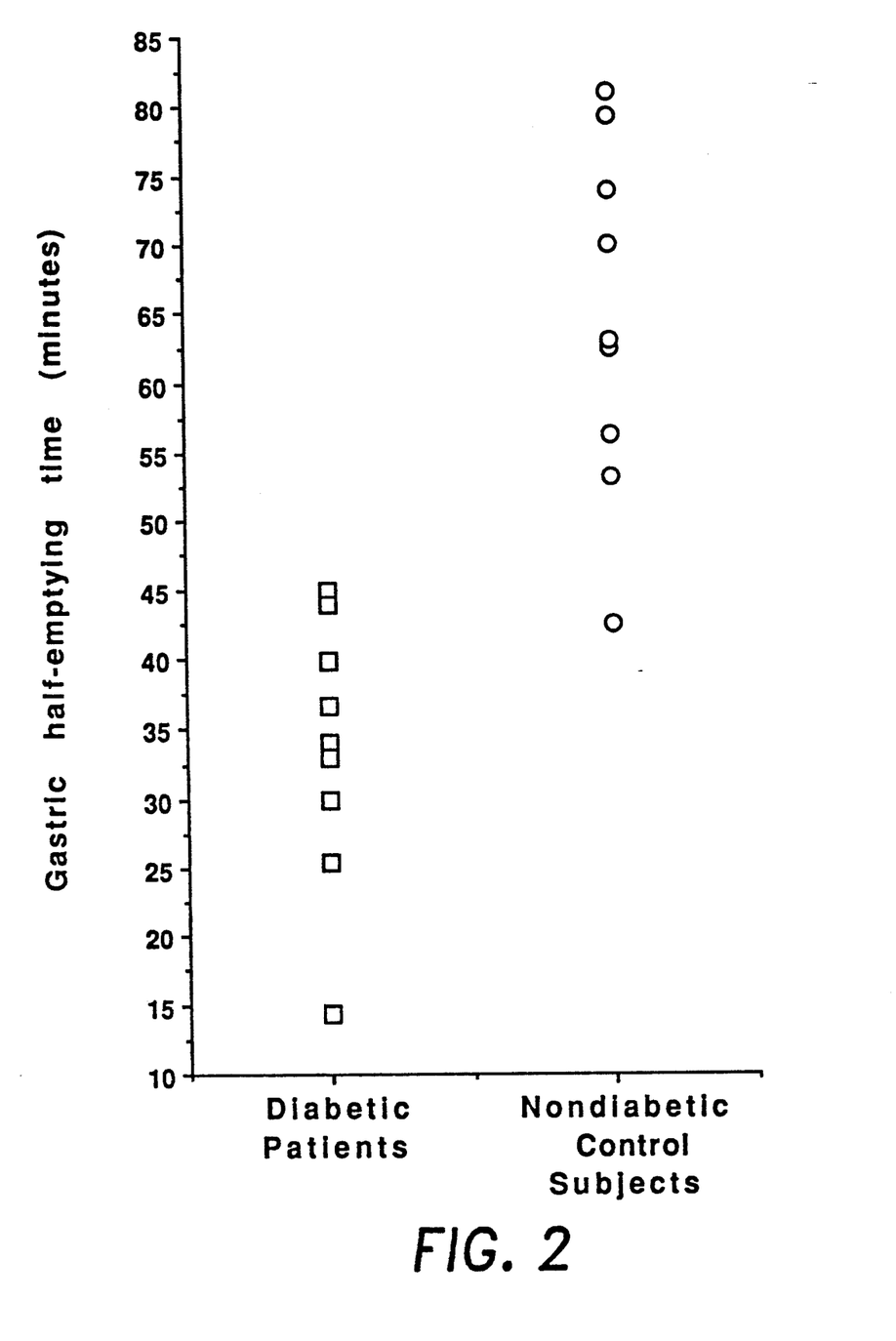
FIG. 2 compares the gastric half-emptying time for subjects with non-insulin dependent diabetes and non diabetics.
Figure 3:
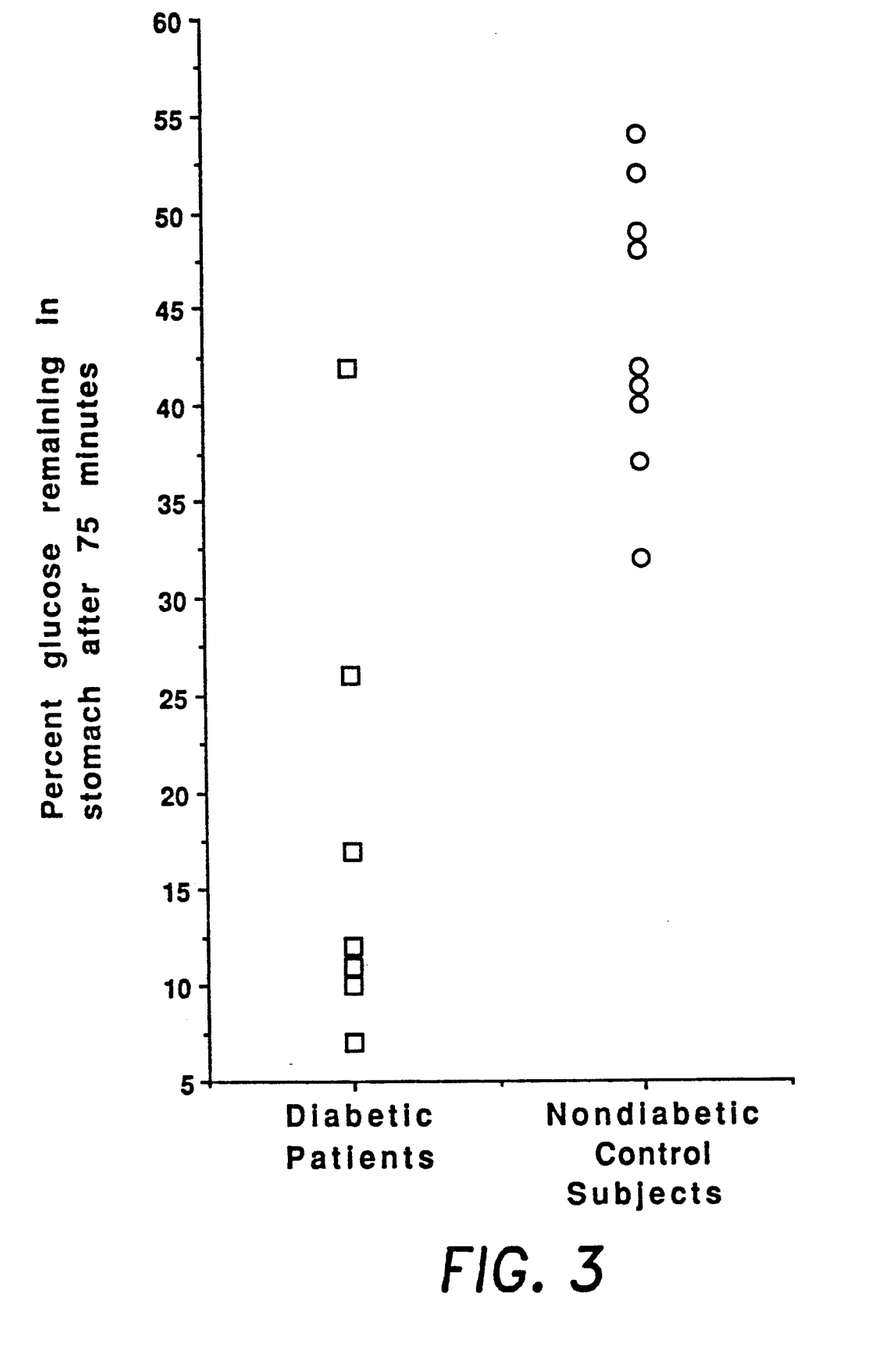
FIG. 3 shows the percent glucose remaining in the stomach 75 min after administration of a glucose solution to non-insulin dependent diabetes mellitus patients and to control patients.

The half emptying time was significantly (P=0.009) shorter for the subjects with non-insulin dependent diabetes (average=32.6 min, SE=5.5) than for the non-diabetics (average=64.3, SE =5.5) as shown in FIGS. 1 and 2. The area under the gastric-emptying curve during the first hour, representing an overall time-weighted average, for the subjects with non-insulin dependent diabetes mellitus was 74% of the area under the curve for the non-diabetics (P=0.016). The area under the curve during the two hours for the subjects with NIDDM was 60% of the area under the curve for the non-diabetics (P=0.002). The half-emptying time and the area under the curve indicate substantially faster emptying for the subjects with NIDDM. The largest mean separation between subjects with NIDDM and non-diabetics occurred at 75 minutes (P=0.004) as shown in FIG. 3.

Figure 4:
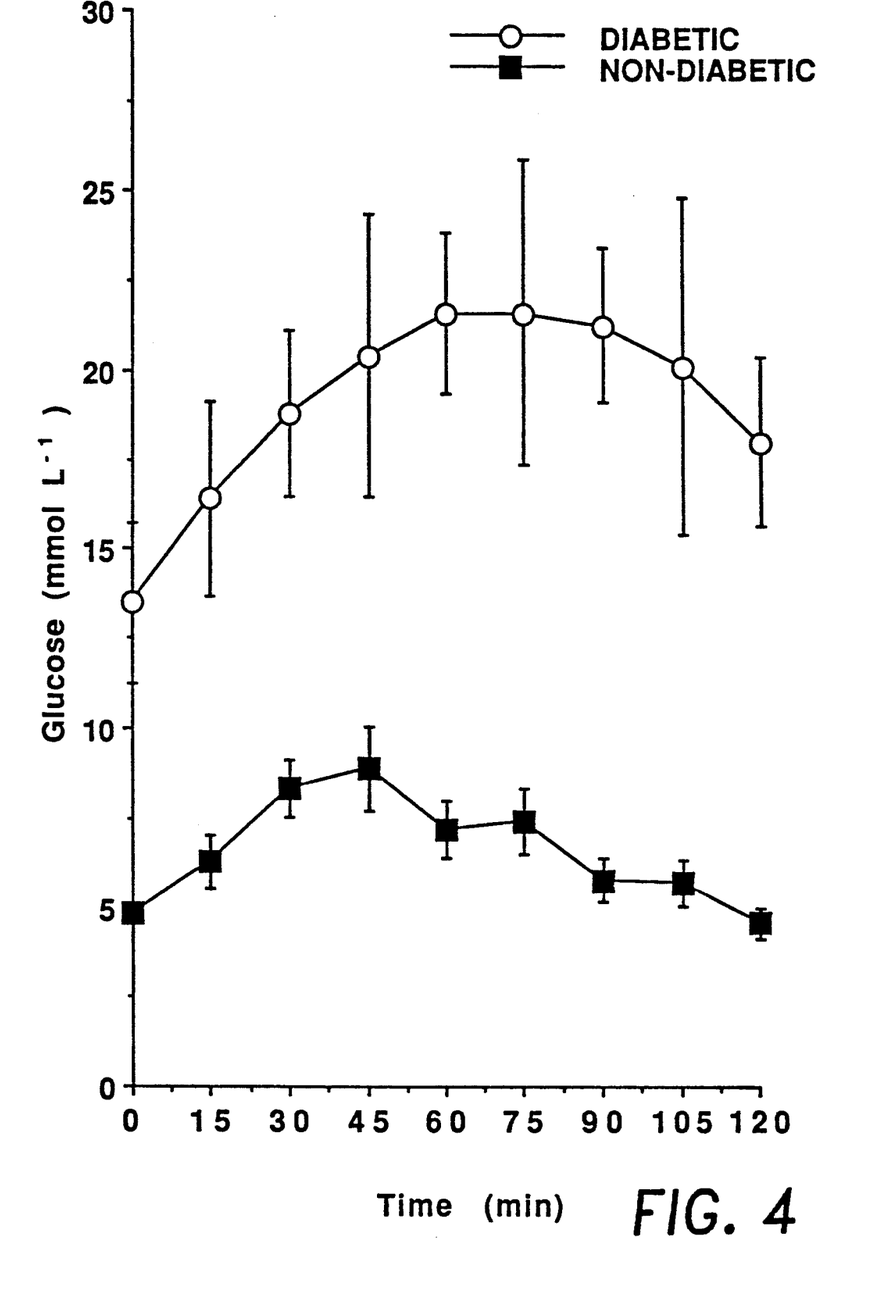
FIG. 4 compares plasma glucose concentrations between subjects with non-insulin dependent diabetes mellitus and controls at 15 min intervals up to 120 min.

The fasting glucose concentrations were significantly different between the subjects with NIDDM and non-diabetics (P=0.009). The glucose concentrations also were different between diabetics and non-diabetics at 15 min intervals as shown in FIG. 4. At other times post ingestion, glucose concentration was not measured on all subjects.

The area under the glucose concentration curve during the first hour, representing an overall time-weighted average, for the subjects with NIDDM was 252% of the area under the curve for the non-diabetics (P=0.006). The area under the curve during the two hours for the subjects with NIDDM was 292% of the area under the curve for the non-diabetics (P=0.003). Even though the subjects with NIDDM had more rapid gastric emptying, their plasma glucose peak was delayed (60–75 min) when compared to the normal controls (45 min).

The average rate of calories emptied into the intestine (calculated using the time of half gastric emptying) by the subjects with NIDDM was 3.1 kcal/min, while non-diabetic controls emptied at a rate of 1.6 kcal/min. The extremes in caloric emptying varied between a diabetic subject emptying at a rate of 7.1 kcal/min and a non-diabetic subject emptying at 1.2 kcal/min.

EXAMPLE 2

Control of Gastric Emptying by Administration of CCK

Two subjects with early NIDDM (diagnosed for less than 2 years) underwent two separate gastric emptying studies. Subjects were Hispanic Americans, ages 37 and 49, both previously diagnosed as diabetic according to current WHO criteria using a 75 g glucose tolerance test (OGTT) with blood sampled fasting and at 2 hr. The one subject on oral hypoglycemic medication discontinued his medication the evening prior to the study. All studies were begun between 7–8 am following a 12 hour fast.

An 18 gauge angiocatheter was placed in one antecubital fossa for blood drawing while another 18 gauge angiocatheter was placed in the other antecubital fossa for a 0.9% (normal saline) infusion (60 ml/min). Gastric emptying studies utilizing a gamma camera (Scintronix USA, Inc., Woburn MA) were performed with a modified 0.62 M (50 g glucose in 450 ml water) glucose solution. This solution has been used previously in gastric emptying studies (9). Approximately 200 μCi of 99 metastable technetium sulfur colloid ($^{99m}$Tc-SC, CIS-US, Bedford, MA) was added and mixed with the glucose solution. The subjects drank the entire glucose solution within 5 min shortly after the $^{99m}$Tc-SC had been added to the solution.

The subjects were then seated at a 90 degree angle in front of a gamma camera. The subjects were instructed to stand at 10 min intervals so that anterior, posterior and left anterior oblique views could be obtained (one minute each) by the camera for a total of 120 min. Images were thus acquired every 10 min. The Scintronix gamma camera was used with a low-energy, all purpose collimator at a 20% window setting centered at 140 keV. The camera was connected to a Medical Data Systems Computer (Ann Arbor, MI). Counts in the stomach region of interest were calculated in each second image. After correcting for radioactive decay, the count rates were converted to a percentage of the maximum count rate recorded.

Blood samples were drawn from the indwelling 18 gauge angiocatheter in the antecubital fossa at 15 min intervals beginning just prior to ingestion of the glucose solution and ending at 120 min. Blood for glucose evaluation was collected in grey-top vacutainer tubes containing potassium oxalate and sodium fluoride. Blood for insulin and C-peptide was collected in red top tubes. Samples for hemoglobin A-1-C, gastric inhibitory polypeptide (GIP) and CCK were collected in lavender top tubes containing EDTA. All glass tubes were from Becton Dickinson Vacutainer Systems, Rutherford, NJ. Glucose analysis were performed on a Paramax instrument (Baxter Healthcare Corp., Irvine, CA). Hemoglobin AIC was performed by the micro column test (Bio-Rad, Hercules, CA 94547).

The C-peptide assay was performed by Smith Kline Bioscience Laboratories, Van Nuys, CA by radioimmunoassay (Diagnostic Products, Los Angeles, CA 90045). The assay for insulin was performed by Smith Kline Bioscience Laboratory, St. Louis, MO by radioimmunoassay (Pharmacia Diagnostics, Fairfield, NJ 07004). Assays for GIP and CCK were performed by radioimmunoassay by the Gastroenterology Unit at Mayo Clinic (Rochester, MN 55905) using in-house kits.

In the first test each subject drank the glucose solution. A gastric emptying study was then performed with simultaneous infusion of normal saline during a two hour period.

The second study was performed 3 days later. Subjects drank the glucose solution and a gastric emptying study was performed with simultaneous infusion of CCK (Kinevac TM, Squibb Diagnostics, Princeton, NJ 08543) at 48 pM/kg/hr.

Both the saline and the CCK solutions were infused using an Abbott/Shaw Life Care TM Pump, Model 4 (Abbott Laboratories, North Chicago, IL 60064). The saline and CCK solutions were delivered by the pump through a vented Abbott/Shaw IV, Lifecare TM pump set (Abbott Hospitals, Inc., North Chicago, IL 60064). The pump was set to deliver 60 ml fluid per hr. The infusate of CCK solution consisted of 3 vials of lyophilized CCK (5 μg each) rehydrated with 5 ml normal saline each. A total of 135 ml of normal saline was added to the rehydrated CCK for a total of 150 ml. The 150 ml was injected into an Empty Evacuated Container (Abbott Laboratories, North Chicago, IL 60064). Infusions of the saline solution for the first test and the CCK solution for the second test were begun 10 min prior to ingestion of the glucose solution.

At the initiation of the study, subject 1 had a hemoglobin AIC level of 4.3% and C-peptide of 4.0 ng/ml. Subject 2 had a hemoglobin AIC level of 9.0% and a C-peptide of 2.9 ng/ml.

In the first test with a controlled saline infusion, plasma glucose levels in subject 1 peaked at 60 min at 272 mg/dl with insulin levels also peaking at 60 min at 111μU/ml. In subject 2 plasma glucose levels were maximal at 45 min at 488 mg/dl while insulin levels remained low, reaching a maximum level of 30 μU/ml at 90 min. Gastric half-emptying time was 25 min for subject I and 15 min for subject 2. CCK levels in subject 1 peaked at 90 minutes at the level of 81.0 pg/ml. GIP levels peaked at 30 min at 608 pg/ml. CCK levels in subject 2 peaked at 30 min at a level of 61 pg/ml. Data are shown in FIGS. 5-9 and Table 1. GIP levels insubject 2 peaked at 30 min at 1169 pg/ml, see FIG. 9.

TABLE 1

Insulin Levels With and Without Simultaneous CCK Administration (μU/ml)

| Time (min) | Subject 1 | | Subject 2 | |
|---|---|---|---|---|
| | No CCK | CCK | No CCK | CCK |
| 0 | 24 | 41 | 19 | 19 |
| 15 | 36 | 36 | 23 | 18 |
| 30 | 64 | 29 | 19 | 18 |
| 45 | 84 | 38 | 24 | 18 |
| 60 | 111 | 28 | 25 | 19 |
| 75 | 98 | 30 | 24 | 18 |
| 90 | 128 | 34 | 30 | 18 |
| 105 | 95 | 32 | 21 | 19 |
| 120 | 82 | 46 | 20 | 19 |

Figure 5:
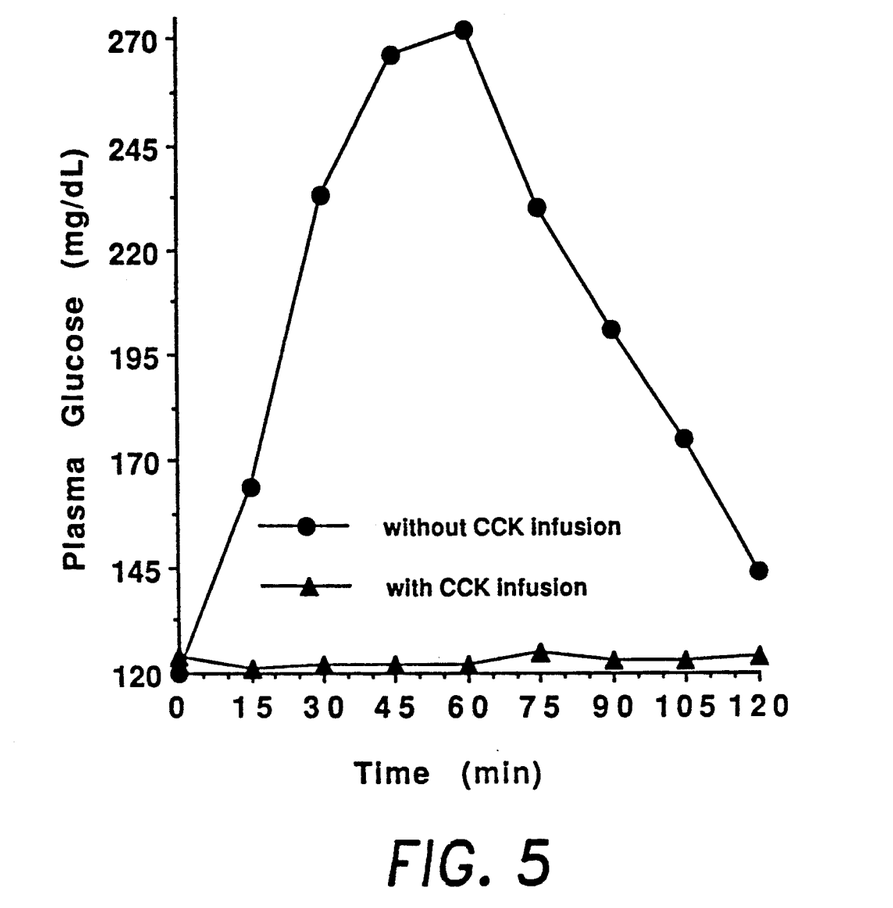
FIG. 5 shows plasma glucose levels in mg/dl over a period of 120 min in subject 1. Plasma glucose levels following ingestion of glucose solution without CCK infusion are indicated by ●. Plasma glucose levels following ingestion of glucose solution with simultaneous CCK infusion are indicated by ▲.
Figure 7:
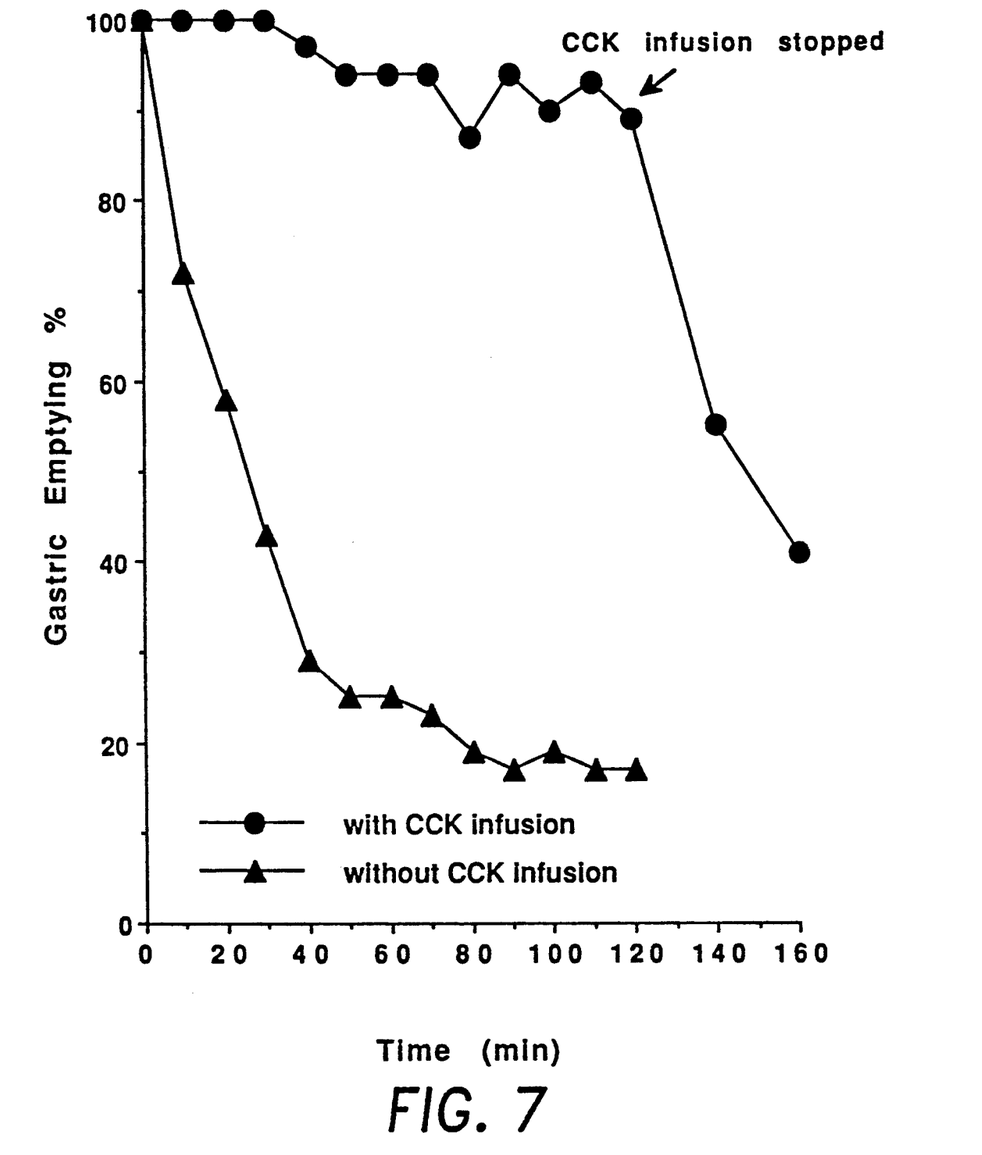
FIG. 7 shows percent of stomach contents emptied in subject 1 (gastric emptying) measured over a period of 160 min. Gastric emptying of glucose solution with simultaneous CCK infusion is represented by ●. Gastric emptying of glucose solution without CCK infusion is represented by ▲.

The effect of CCK infusion on gastric emptying was studied in each subject. In subject 1, plasma glucose levels remained steady throughout the two hour study and ranged from 121 mg/dl to 125 mg/dl as shown in FIG. 5. Insulin levels also remained in a narrow range (28-46 μU/ml, Table 1). The gastric emptying time, as indicated in FIG. 7, was markedly delayed with only 11% of the total volume emptying after 120 min. At the end of the two hr period, the CCK infusion was stopped and a more rapid gastric emptying pattern ensued. One hundred forty min after ingestion of the glucose solution, 55% of the total volume remained in the stomach, 41% after 160 min, FIG. 7. CCK levels peaked at 120 min post ingestion of the glucose solution. GIP levels peaked at 30 min.

Figure 6:
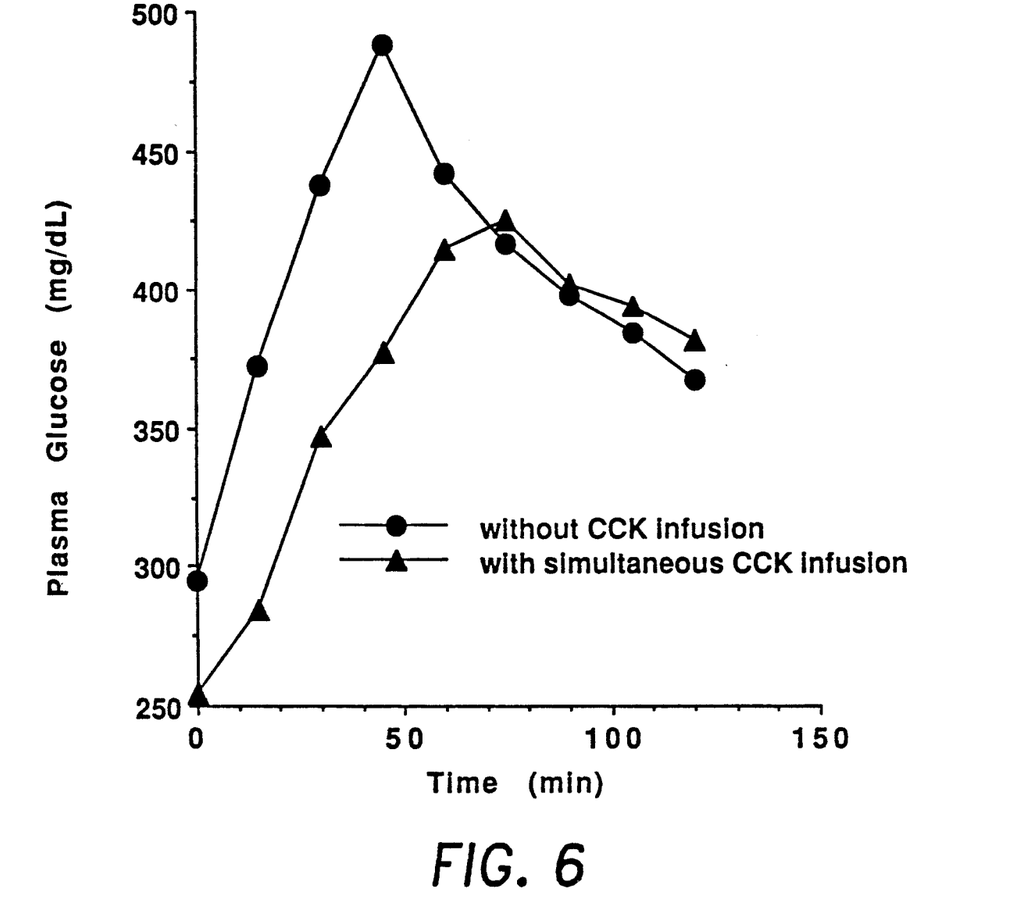
FIG. 6 shows plasma glucose levels in mg/dl over a period of 120 min in subject 2. Plasma glucose levels following ingestion of glucose solution without CCK infusion are indicated by ●. Plasma glucose levels following ingestion of glucose solution with simultaneous CCK infusion are indicated by ▲.
Figure 8:
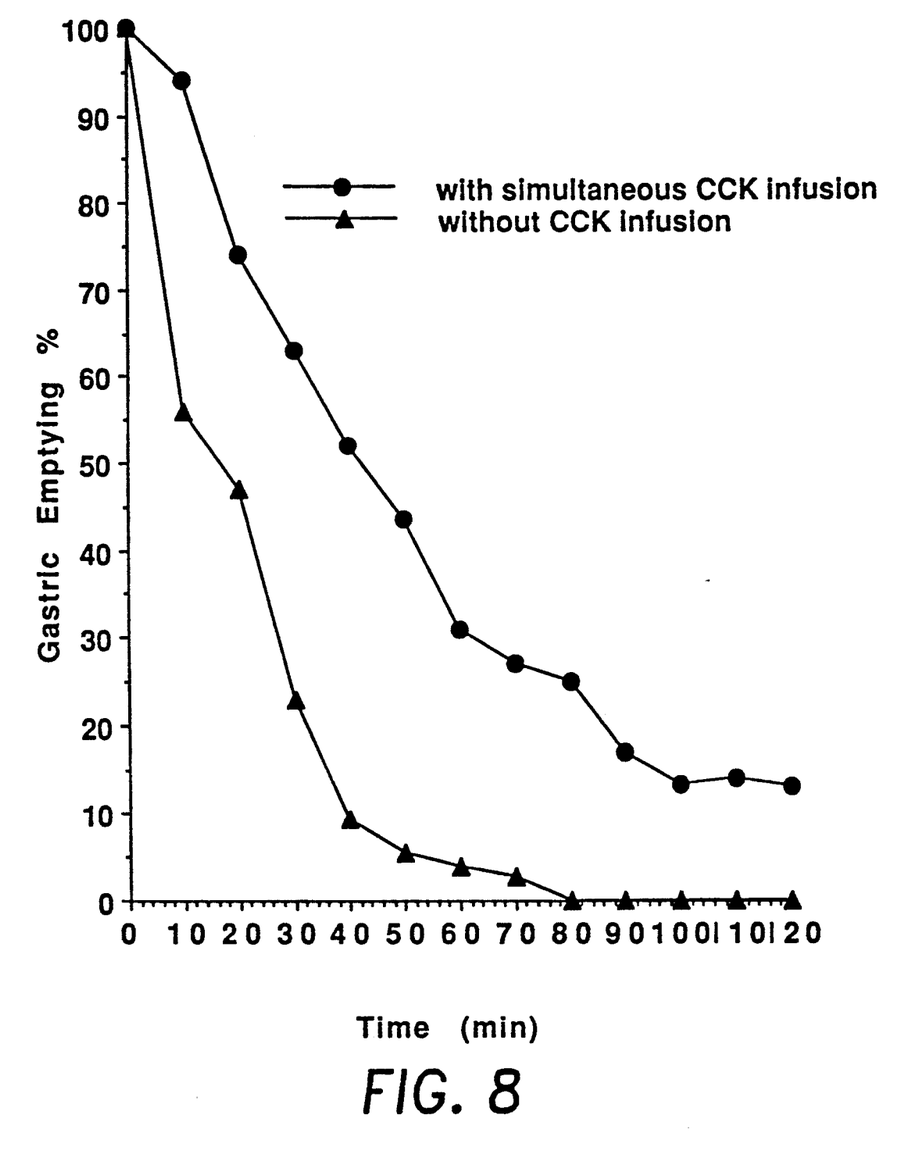
FIG. 8 shows percent of stomach contents emptied in subject 2 (gastric emptying) measured over a period of 120 min. Gastric emptying of glucose solution with simultaneous CCK infusion is represented by ●. Gastric emptying of glucose solution without CCK infusion is represented by ▲.
Figure 9A:
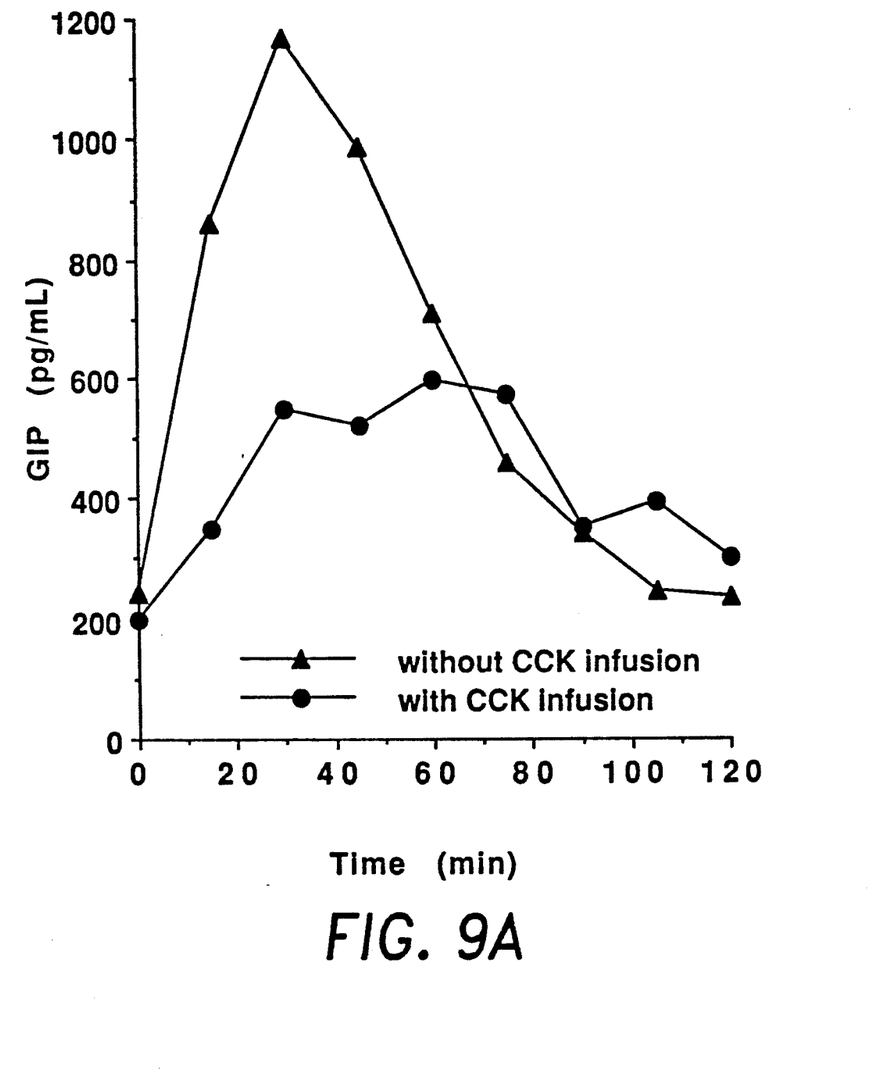
FIG. 9A and FIG. 9B show the effect of CCK infusion on GIP levels in two subjects measured over a period of 120 minutes Gastric emptying of glucose solution without CCK is represented by ▲. Gastric emptying of glucose solution with simultaneous CCK infusion is represented by ●.
Figure 9B:
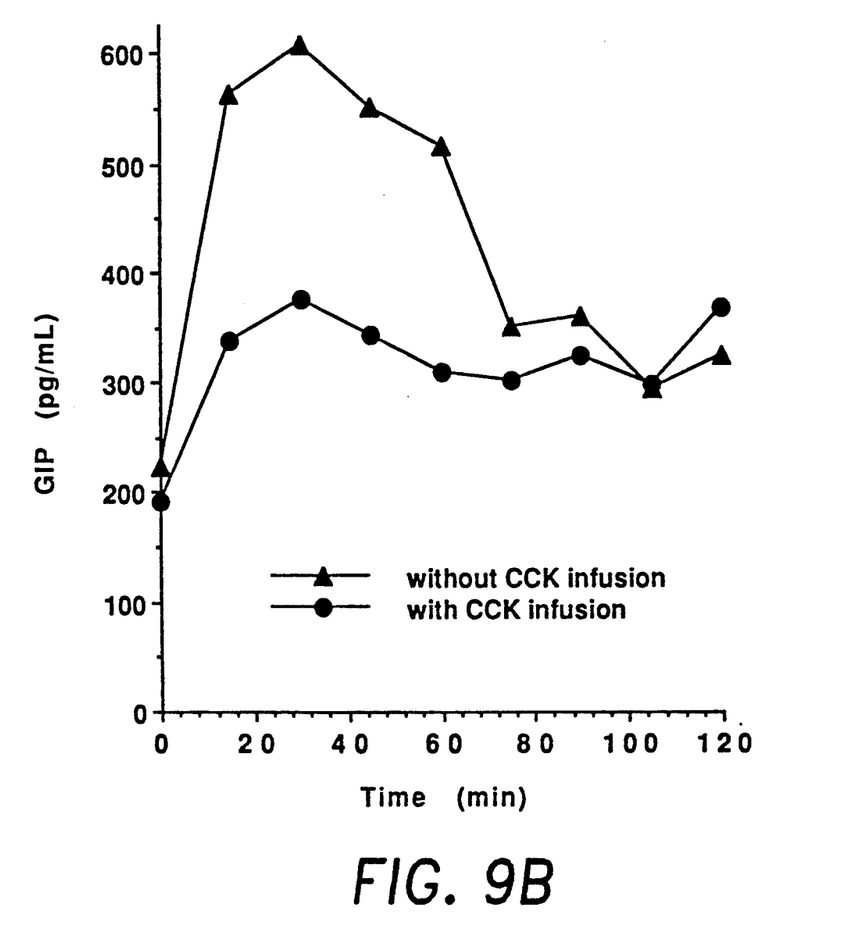

In subject 2, CCK infusion delayed peak plasma glucose levels by approximately 30 min from 45 to 75 min as shown in FIG. 6. Insulin levels were low throughout the two hr test period, ranging between 18-19 μU/ml. The gastric half-emptying time was 43 min as shown in FIG. 8. CCK levels peaked at 105 min post ingestion of the glucose solution. GIP levels peaked at 60 min. Differences in GIP kinetics before and after CCK administration are shown in FIG. 9.

The present invention has been described in terms of particular embodiments found by the inventors to comprise preferred modes of practice of the invention. It will be appreciated by those of skill in the art that in light of the present disclosure numerous modifications and changes can be made without departing from the intended scope of the invention. For example, other methods than drugs might be used to delay gastric emptying, such as cellulose derivatives and gastric bubbles. All such modifications are intended to be within the scope of the claims.

REFERENCE

The references listed below are incorporated herein by reference to the extent they supplement, explain, provide a background for or teach methodology, techniques and/or compositions employed herein.

1. Thompson, D. G., Wingate, D. L., Thomas, M. and Harrison, D., Gastroenterology 82, 51-55 (1982).
2. Brener, W., Hendrix, T. R., MoHugh, P. R., Gastroenterology 85, 76-82 (1983).
3. Keshavarzian, A., Iber, F. L., Vaeth, J., Am. J. Gastroenterology 82, 29-35 (1987).
4. Campbell, I. W., Heading, R. C., Tothill, P., :Buist, T. A. S., Ewing, D. J., Clarke, B. F., Gut 18, 462-467 (1977).
5. Horowitz, M., Harding, P. E., Maddox, A. F. et al., Diabetologia 32, 151-159 (1989).
6. Smout, J. J. P. M., Z. Gastroenterol. 24/supp 2, 45-54 (1986).
7. Pellegrini, C. A., Broderick, W. C., VanDyke, D. and Way, L. W., Am. J. Surg. 145, 143-151 (1983).
8. Akkermans, L. M. A., Houghton, L. A. and Brown, N. J., Scand. J. Gastroenterol Suppl. 24, 27-31 (1989).
9. Schwartz, J. G., Phillips, W. T. and Aghebat-Khairy, B. Clin. Chem. 36, 125 (1990).
10. Liddle, R. A., Fed. Res. in Progress, Natl. Inst. Diabetes and Dig. Dis., 1990.
11. Chaudhuri, T. K and Fink, S., Am J. Gastroenterology 85, 223-231 (1990).
12. Liddle, R. A. et al., J. Clin. Invest. 77, 992 (1986).
13. Liddle, R. A., Rushakoff, R. J., Morita, E. T., Beccaria, L., Carter, J. D. and Goldfine, I. D., J. Clin Invest. 81. 1675-1681 (1988).
14. Jenkins, D. J. A., Thomas, M. S., Wolever, M. S., Ocana, A. M., Vuksan, V., Cunnane, S. C., Jenkins, M., Wong, G. S., Singer, W., Bloom, S. R., Blendis, L. M. and Josse, R. G., Diabetes 39, 775-780 (1990).

What is claimed is:

1. A method of maintaining the following glucose metabolic indicators at or near normal levels; blood glucose, C-peptide, insulin levels at fasting and during oral glucose tolerance tests, hemoglobin AIC, insulin resistance, GIP levels and CCK levels, in an individual having an early noninsulin-dependent diabetic condition and exhibiting rapid gastric emptying comprising administering to the individual a therapeutically effective dose of cholecystokinin.

2. The method of claim 1 wherein the early noninsulin-dependent diabetic condition is an impaired glucose tolerance, hyperinsulinemia or insulin resistance.

3. The method of claim 1 wherein the early noninsulin-dependent diabetic condition is borderline diabetes, characterized by abnormally high blood glucose and or insulin, insulin resistance and optionally characterized by glycosuria or increased thirst.

4. The method of claim 1 wherein the therapeutically effective dose of choleycslokinin comprises an injectable pharmaceutical carrier.

* * * * *